(12) United States Patent
Krupnick

(10) Patent No.: US 9,770,307 B2
(45) Date of Patent: Sep. 26, 2017

(54) COVER ASSEMBLY FOR A STETHOSCOPE AND A DISPENSER KIT

(71) Applicant: Jon Krupnick, Asheville, NC (US)

(72) Inventor: Jon Krupnick, Asheville, NC (US)

(\*) Notice: Subject to any disclaimer, the term of this patent is extended or adjusted under 35 U.S.C. 154(b) by 108 days.

(21) Appl. No.: 13/923,487

(22) Filed: Jun. 21, 2013

(65) Prior Publication Data

US 2016/0338790 A1    Nov. 24, 2016

(51) Int. Cl.
*A61B 7/02* (2006.01)
*A61B 46/10* (2016.01)
*A61B 50/30* (2016.01)

(52) U.S. Cl.
CPC ............... *A61B 46/10* (2016.02); *A61B 7/02* (2013.01); *A61B 50/30* (2016.02)

(58) Field of Classification Search
CPC ............. A61L 46/10; A61L 50/30; A61L 7/02
USPC ........................................................ 181/131
See application file for complete search history.

(56) References Cited

U.S. PATENT DOCUMENTS

| | | | | |
|---|---|---|---|---|
| 5,949,032 A * | 9/1999 | Wurzburger | ............ | A61B 7/026 181/131 |
| 6,009,971 A * | 1/2000 | Weidman | ................. | A61B 7/02 181/131 |
| 6,041,889 A * | 3/2000 | Stark | ........................ | A61B 7/02 181/131 |
| 6,499,560 B1 * | 12/2002 | Lang | ......................... | A61B 7/02 181/131 |
| 7,117,971 B1 * | 10/2006 | Cornacchia | ............... | A61B 7/02 181/131 |
| 7,469,769 B1 * | 12/2008 | Hmayakyan | ............. | A61B 7/02 181/131 |
| 2005/0257996 A1 * | 11/2005 | Brown | ...................... | A61B 7/02 181/131 |
| 2007/0045039 A1 * | 3/2007 | Agahi | ....................... | A61B 7/02 181/131 |
| 2008/0230303 A1 * | 9/2008 | Weidman | ................. | A61B 7/02 181/131 |
| 2008/0257637 A1 * | 10/2008 | Miller | ....................... | A61B 7/02 181/131 |
| 2009/0014232 A1 * | 1/2009 | Hirsch | ...................... | A61B 7/02 181/131 |
| 2009/0145685 A1 * | 6/2009 | Hmayakyan | ............. | A61B 7/02 181/131 |
| 2010/0212995 A1 * | 8/2010 | Hmayakyan | ............. | A61B 7/02 181/131 |

\* cited by examiner

*Primary Examiner* — Forrest M Phillips
(74) *Attorney, Agent, or Firm* — Malin Haley DiMaggio & Bowen, P.A.

(57) ABSTRACT

A cover assembly for use with a stethoscope is provided and the cover assembly includes a head overlay element and a pre-deployment protection component. The head overlay element is operable to overlay the stethoscope head in a deployed disposition of the assembly in which the cover assembly is releasably retained on the stethoscope. The pre-deployment protection component advantageously protects the head overlay element against the detrimental effects of moisture, debris, or other substances that would degrade the operation of either the cover assembly or the stethoscope once the cover assembly is deployed on the stethoscope.

8 Claims, 15 Drawing Sheets

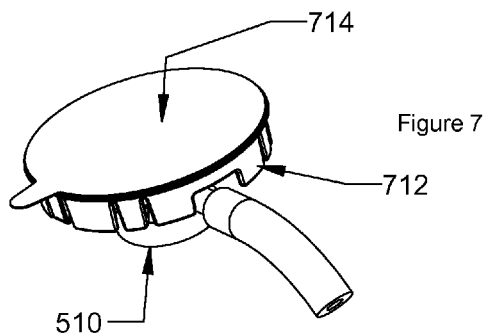
Figure 7
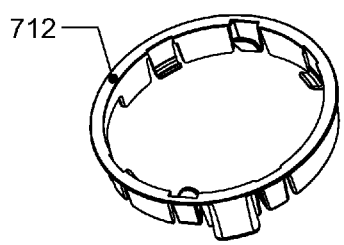
Figure 8
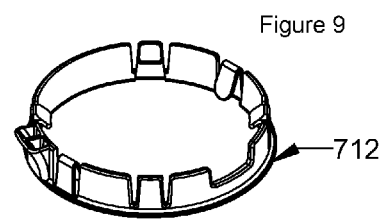
Figure 9
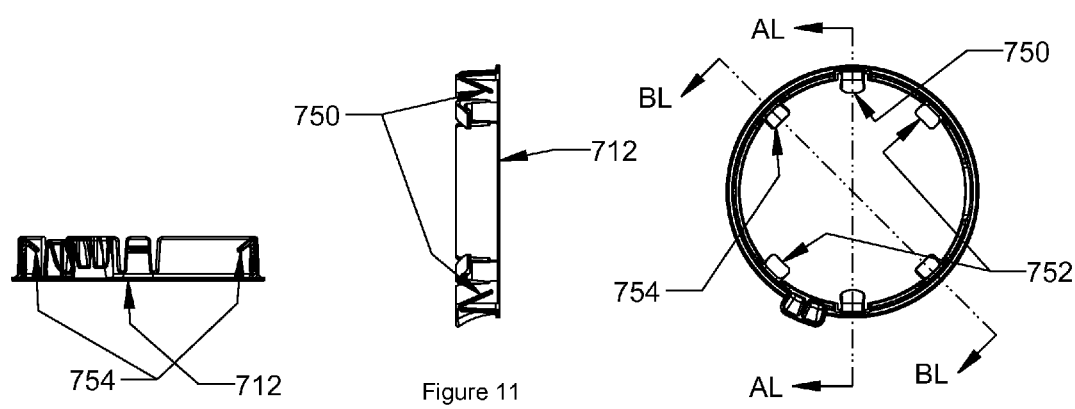
Figure 12
Figure 11
Figure 10

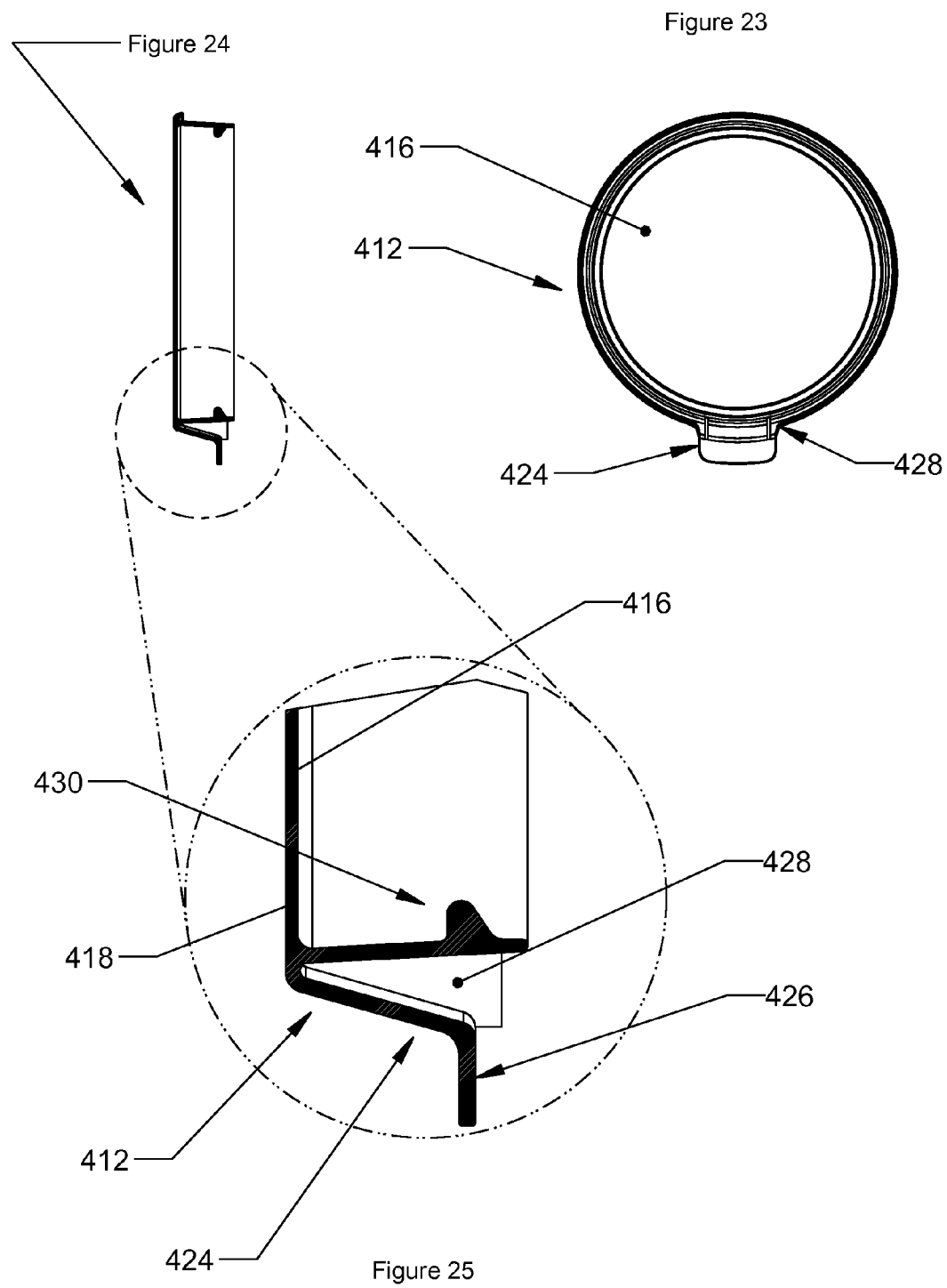

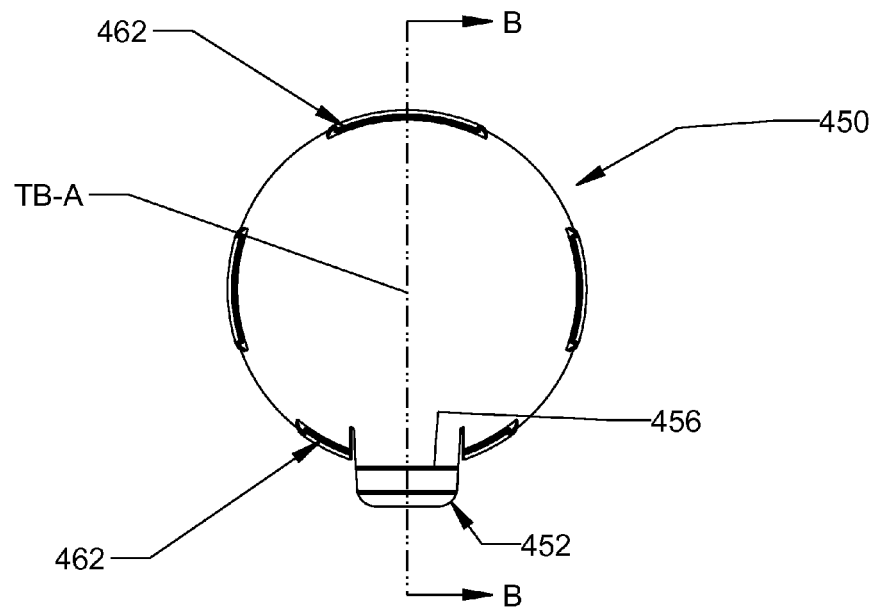
Figure 28
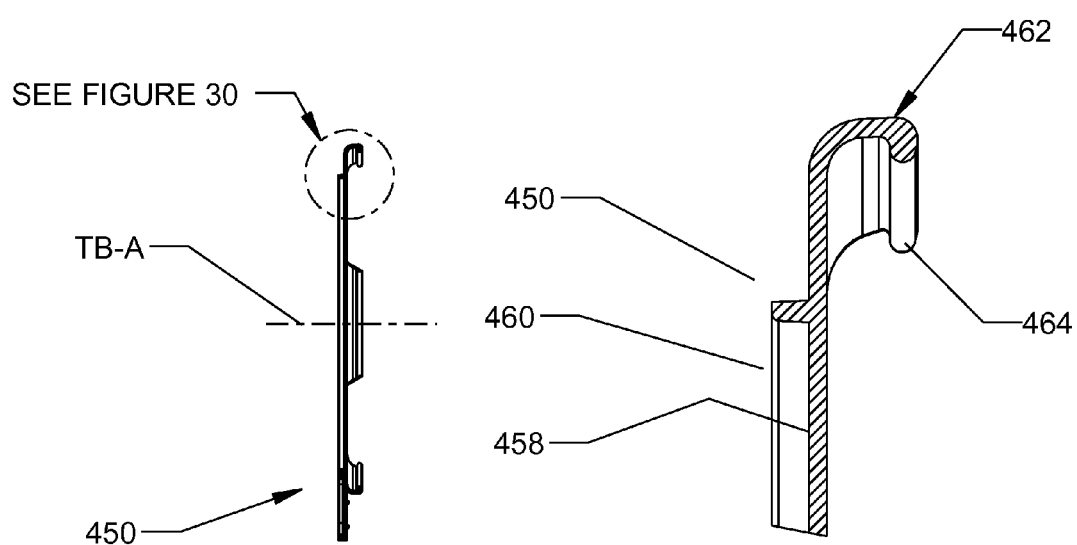
Figure 29
Figure 30

COVER ASSEMBLY FOR A STETHOSCOPE AND A DISPENSER KIT

BACKGROUND OF THE INVENTION

The present invention generally relates to a cover for a stethoscope and relates more particularly to a convenient and rapidly deployable stethoscope cover that provides a clean contact surface between a patient and the stethoscope.

With reference to FIGS. 1-3, a prior art hygienic protection element is shown that is disclosed in the patent publication WO 01/49180A1 (Inventor: Roberto Semani) and, according to the patent publication WO 01/49180A1, this hygienic protection element 10 is able to be applied to a medical instrument to prevent direct contact of the instrument and the patient. According to the patent publication WO 01/49180A1, the hygienic protection element 10 is able to be applied to a phonendoscope/stethoscope 13, is a single-use type, and is advantageously supplied in individual sterile packages.

According to the patent publication WO 01/49160A1, the hygienic protection element 10 is comprised of a thin film 11, made of a substantially adherent and non-toxic material, associated to the main surface of a flexible support made, for example, of shiny paper. The film 11 is advantageously made of plastic material, for example polypropylene (PP), polyethylene (PE) or polymethylpentene (PMP). The film 11 is a size and shape suitable for it to be applied to the part of the medical instrument which comes into contact with the patients body. The film may be circular in shape and can be applied through adherence to the lower side of the resounding chamber 13a of the phonendoscope/stethoscope 13. The flexible support has the same size and shape as the film 11 and comprises a central portion, circular in shape and with a diameter which is larger than the resounding chamber 13a of the phonendoscope/stethoscope 18, and a perimeter portion of an annular shape.

The patent publication WO 01/49180A1 discloses that the hygienic protection element 10 is applied to the phonendoscope/stethoscope 13 in the following manner. The central portion of the flexible support 18 is removed, and the corresponding uncovered zone of the film rests on the lower side of the resounding chamber 13a of the phonendoscope/stethoscope 13. The film 11 is firstly disposed to adherently contact the perimeter portion of the resounding chamber 13a, and subsequently wound laterally until it adheres well to the instrument. In this condition, where the film 11 is taut on the lower side of the resounding chamber 13a of the phonendoscope/stethoscope 13, while it is raised from the instrument in correspondence with the perimeter portion, the phonendoscope/stethoscope 13 can be used. At the end of the examination, the hygienic protection element 10 can be removed easily by gripping the perimeter portion, which facilitates this operation, since it does not adhere to the resounding chamber.

While patent publication WO 01/49180A1 discloses a cover for a stethoscope head in the form of a hygienic protection element, the installation of this prior art stethoscope cover requires that a portion of the cover be folded against, and adhered to, the outer side of the resounding chamber of the stethoscope. Accordingly, there is room for improvement in the art of stethoscope covers for a stethoscope cover that reduces the complexity of installing the stethoscope cover on the stethoscope.

SUMMARY OF THE INVENTION

A need therefore exists for a cover assembly for a stethoscope that eliminates or diminishes the disadvantages and problems described above.

One object of the present invention is to provide a cover assembly for a stethoscope that can be installed on the stethoscope in a simple manner involving less complex or fewer steps than those required in the installation of prior art stethoscope covers.

A further object of the present invention is to provide a cover assembly for a stethoscope that is preferably convenient to remove from the stethoscope.

Yet another object of the present invention is to provide a cover assembly for a stethoscope that, when stored prior to its deployment, is advantageously protected against the detrimental effects of accumulating moisture, debris, or other substances that would degrade the operation of either the cover assembly or the stethoscope once the cover assembly is deployed on the stethoscope.

An additional object of the present invention is to provide a dispenser kit for dispensing cover assemblies for stethoscopes.

According to one aspect of the present invention, there is provided a cover assembly for use with a stethoscope having a stethoscope head with a membrane, a sound transmission tube extending from the stethoscope head, and an ear placement piece connected to the sound transmission tube. The cover assembly includes a head overlay element and a pre-deployment protection component. The head overlay element is operable to overlay the stethoscope head in a deployed disposition of the assembly in which the assembly is releasably retained on the stethoscope, the head overlay element having an element axis, a head facing surface and a stand off surface with the head facing surface of the head overlay element being axially intermediate the stethoscope head and the stand off surface of the head overlay element in the deployed disposition of the assembly. The pre-deployment protection component is operably associated with the head overlay element and operable to discourage the deposition of certain substances on the head overlay element and the pre-deployment protection component being located relative to the head overlay element such that the stand off surface of the head overlay element is axially intermediate the pre-deployment protection component and the head facing surface of the head overlay element.

The present invention is generally directed towards a cover assembly for a stethoscope and a dispenser kit. The principles of the present invention, however, are not limited to the herein disclosed embodiments of these articles. Additionally, to assist in the description of the dispenser kit, words such as top, bottom, front, rear, right and left may be used to describe the accompanying figures, which may be but are not necessarily drawn to scale. It will be appreciated that the dispenser kit can also be oriented in a variety of desired positions and/or orientations.

BRIEF DESCRIPTION OF THE DRAWINGS

Other features and advantages of the invention will become apparent to those skilled in the art upon review of the following detailed description, claims, and drawings.

FIG. 7, which is a top perspective view of the cover assembly deployed on the stethoscope head with the pre-deployment protection component not yet removed from the annularly shaped planar disc of the head overlay element;

FIG. 8 is an enlarged perspective view of this one configuration of the rim of the head overlay element;

FIG. 9 is an enlarged perspective view of this one configuration of the rim of the head overlay element;

FIG. 10 is a top plan view of the one configuration of the rim of the head overlay element shown in FIGS. 8 and 9;

FIG. 11 is a sectional view of the one configuration of the rim of the head overlay element shown in FIG. 10 taken along lines AL-AL, shows first pair of diametrically opposed locking tabs;

FIG. 12 is a sectional view of the one configuration of the rim of the head overlay element shown in FIG. 10 taken along lines BL-BL;

FIG. 23 is a bottom plan view of the head overlay element;

FIG. 24 is a sectional side view of the head overlay element shown in FIG. 23 take along Line A-A;

FIG. 25 is an enlarged sectional view of a portion of the head overlay element shown in FIG. 24;

FIG. 28 is a bottom plan view of the pre-deployment protection component;

FIG. 29 is a sectional side view of the pre-deployment protection component shown in FIG. 28 taken along line B-B;

FIG. 30 is an enlarged side view of a portion of the pre-deployment protection component shown in FIG. 29;

DETAILED DESCRIPTION OF AN EMBODIMENT

Figure 5:
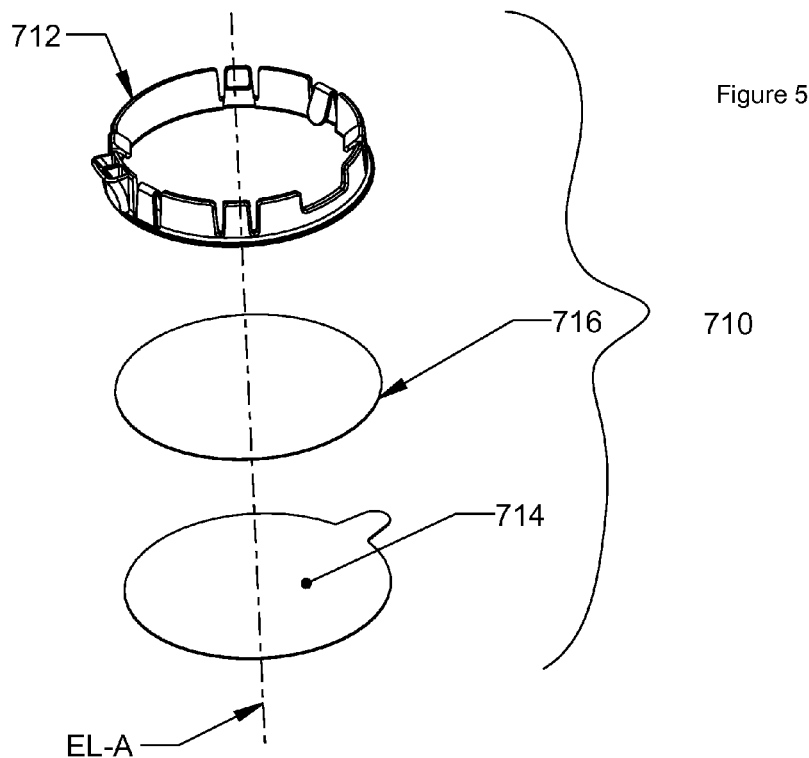
FIG. 5 is an exploded perspective view of one embodiment of the cover assembly of the present invention.

Reference is had to FIG. 5, which is an exploded perspective view of one embodiment of the cover assembly of the present invention, and wherein it can be seen that a cover assembly generally designated as a cover assembly 710 is configured for use with a stethoscope or the type having a stethoscope head with a membrane, a sound transmission tube extending from the stethoscope head, and an ear placement piece connected to the sound transmission tube. The cover assembly 710 includes a head overlay element 712 and a pre-deployment protection component 714.

The cover assembly 710 offers a number of benefits to both the person deploying the stethoscope to monitor a medical condition of a patient and the person—i.e., a patient in a medical setting—being monitored via deployment of the stethoscope. For example, as will be more described in more detail herein, the cover assembly 710 provides a convenient reminder to the person deploying the stethoscope—hereinafter referred to as the health care assessor—that the stethoscope is being deployed in a fresh monitoring situation and the health care assessor can then take the opportunity to ensure that the stethoscope head is clean, dry, and otherwise ready for placing into contact with the patient. Also, the cover assembly 710 provides an ergonomically agreeable configuration for the health care assessor to orient the stethoscope relative to the respective body portion of the person being monitored and to maintain the stethoscope in the properly oriented position while the health care assessor operates the stethoscope in a conventional manner to monitor a medical condition.

Figure 1:
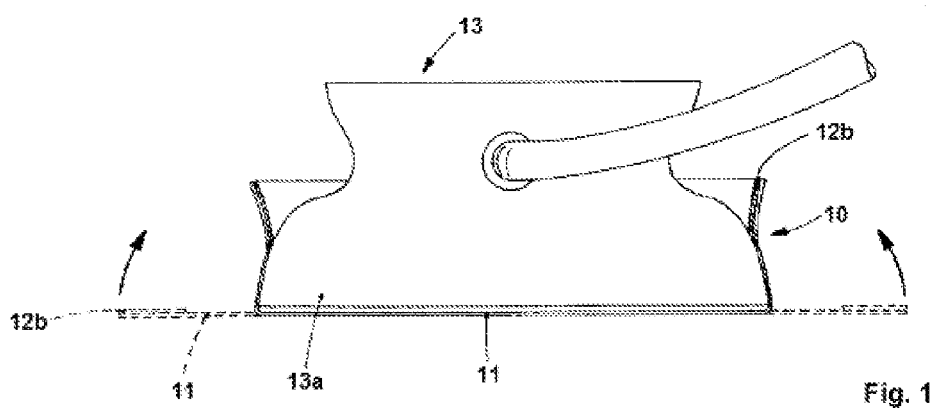
FIG. 1 is a party sectioned side view of a prior art hygienic protection element of applied to a phonendoscope/stethoscope.
Figure 2:
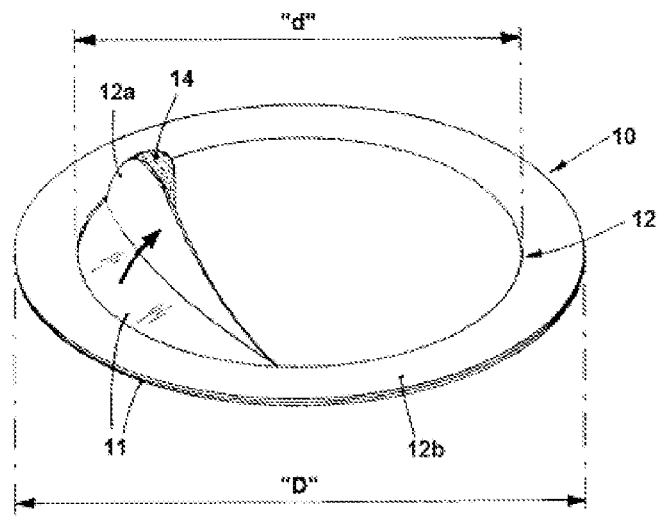
FIG. 2 is a three dimensional view of the prior art hygienic protection element shown in FIG. 1.
Figure 3:
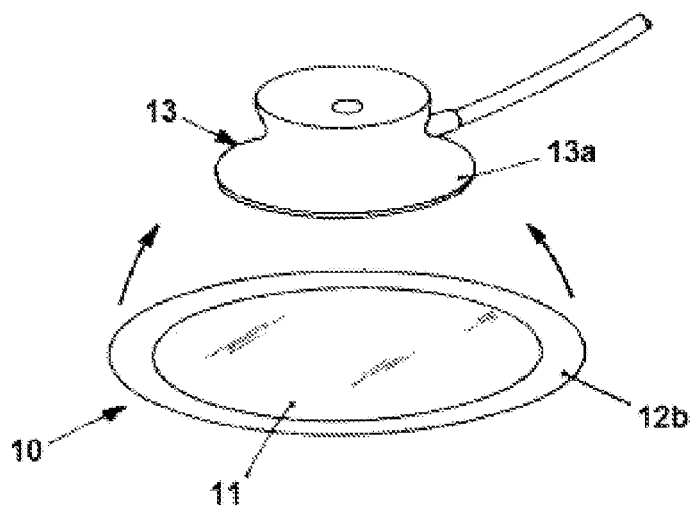
FIG. 3 shows one step in the application of the prior art hygienic protection element shown in FIG. 1 onto a phonendoscope/stethoscope.
Figures 4A, 4B:
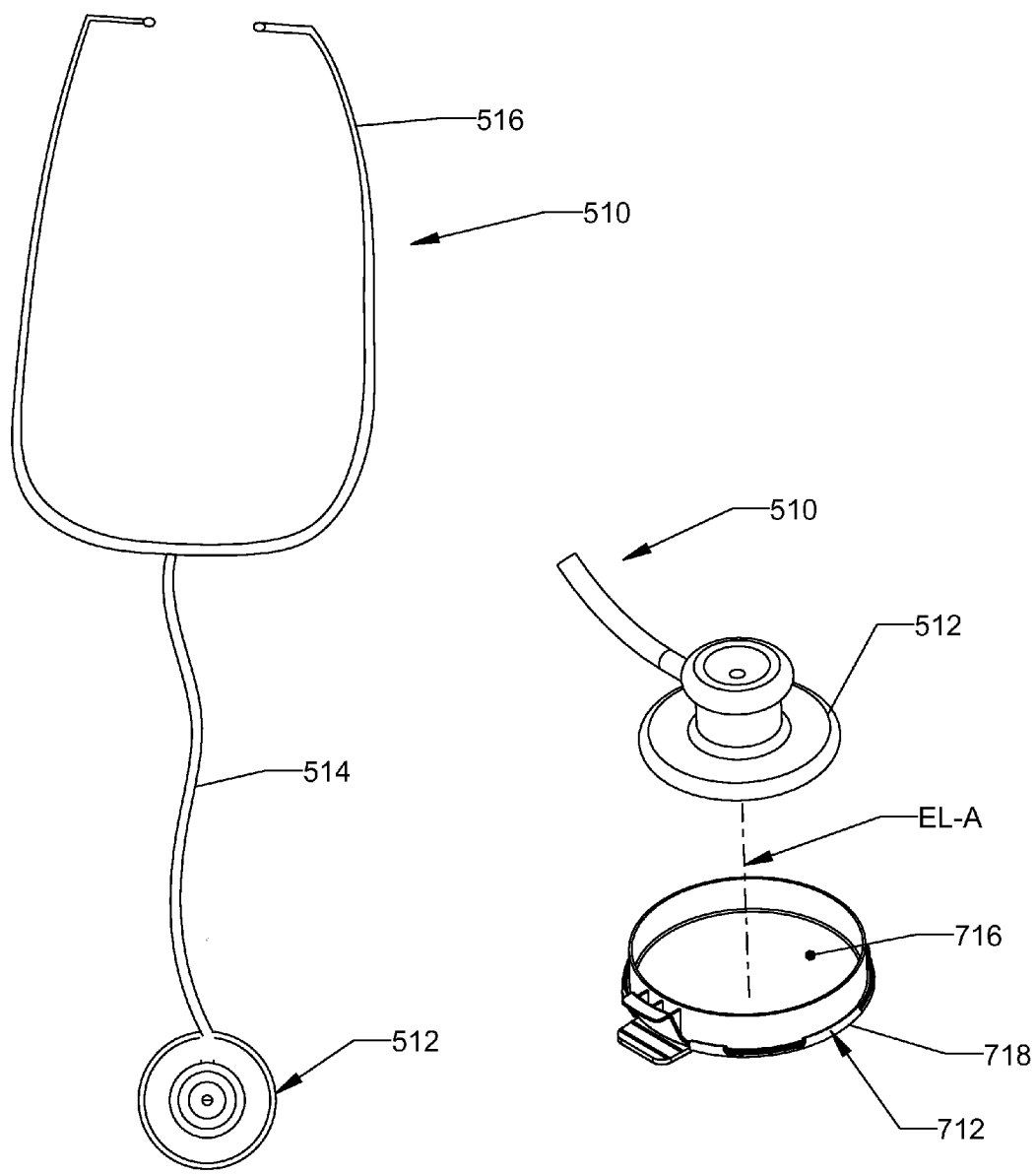
FIG. 4A is a perspective view of a stethoscope.
FIG. 4B is an enlarged perspective view of the stethoscope shown in FIG. 4A and a unit of one embodiment of the cover assembly of the present invention disposed on the stethoscope head.

As noted, the cover assembly 710 offers a number of benefits when deployed on a stethoscope and here is a brief description of the deployment of the cover assembly 710 on a stethoscope. Reference is had to FIG. 4A, which is a perspective view of a stethoscope, hereinafter designated as a stethoscope 510, and FIG. 4B, which is an enlarged perspective view of the stethoscope shown in FIG. 4A and a unit of one embodiment of the cover assembly of the present invention disposed on the stethoscope head. The cover assembly 710 is shown in FIG. 4B in a preliminary alignment position with a stethoscope head 512 of the stethoscope 510 just prior to installation of the cover assembly 710 into its deployed disposition on the stethoscope head 512. In addition to the stethoscope head 512 (sometimes referred to in the art as a stethoscope bell), the stethoscope 510 has a connector tube 514 extending from the stethoscope head 512, and two ear tubes 516 extending from the connector tube 514.

Accordingly, the cover assembly 710 comprising the head overlay element 712 is operable to overlay the stethoscope head 512 in the deployed disposition of the cover assembly 710 in which the cover assembly 710 is releasably retained on the stethoscope 510. The head overlay element 712 is centered on an element axis EL-A and includes a rim that delimits an annular ring surface and that can be formed, for example, as a single piece injection molded plastic component. The interior of the rim of the head overlay element 712 is empty but the head overlay element 712 includes a very thin annularly shaped planar disc having one side that delimits a head facing surface 716 of the head overlay element 712 and an opposite side that delimits a stand off surface 718. This very thin annularly shaped planar disc is secured to the rim of the head overlay element 712 via, for example, a bead of adhesive or via heat bonding or welding. This very thin annularly shaped planar disc may be formed, for example, of a suitable polymeric material, a fiber reinforced material, or any other material that preferably acts in the manner of a very thin membrane in that it permits adequate sound transmission therethrough so as to not substantially interfere with the operation of the stethoscope head 512. The head facing surface 716 of the head overlay element 712 is axially intermediate the stethoscope head 512 and the stand off surface 718 of the head overlay element 712 in the deployed disposition of the cover assembly 710.

Figure 6:
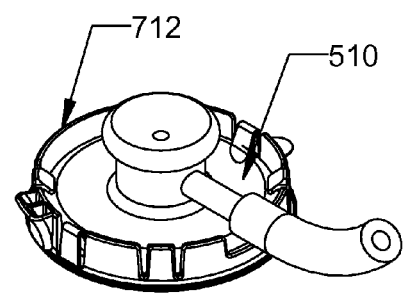
FIG. 6 is a top perspective view of the cover assembly in its deployed disposition on the stethoscope head.

The cover assembly 710 further includes a pre-deployment protection component 714 that may be formed of a very thin planar material and this pre-deployment protection component 714 is configured in correspondence with the very thin annularly shaped planar disc of the head overlay element 712 such that the pre-deployment protection component 714 completely covers and overlays the very thin annularly shaped planar disc of the head overlay element 712 and, additionally, includes a pull tab extension that can be gripped between a users thumb and forefinger to remove or peel off the pre-deployment protection component 714 from the very thin annularly shaped planar disc of the head overlay element 712. The pre-deployment protection component 714 may be formed, for example, of a suitable polymeric material, a fiber reinforced material, or any other material that permits the pre-deployment protection component 714 to perform its function of hygienically protecting the annularly shaped planar disc of the head overlay element 712. Depending on the material composition of the pre-deployment protection component 714, the pre-deployment protection component 714 can be releasably secured to the annularly shaped planar disc of the head overlay element 712 via a static cling-type releasable securement. As seen in FIG. 6, which is a top perspective view of the cover assembly 710 in its deployed disposition on the stethoscope head 510, the stethoscope head is seated within the rim of the head overlay element 712 and the rim applies a slight radially inwardly directed compressive force on the stethoscope head that serves to releasably retain the cover component 710 on the stethoscope head. The nature of the securement of the rim of the head overlay element 712 on the stethoscope head is selected with a view to avoiding acoustic dampening that would distort or interfere with the acoustic performance of the stethoscope 510. Accordingly, the securement of the rim of the head overlay element 712 on the stethoscope head will typically be a relatively loose fit. The pre-deployment protection component 714 can be removed from the annularly shaped planar disc of the head overlay element 712 prior to the deployment of the cover assembly 710 on the stethoscope head 510 or after the deployment of the cover assembly 710 on the stethoscope head 510, as seen in FIG. 7, which is a top perspective view of the cover assembly 710 deployed on the stethoscope head 510 with the pre-deployment protection component 714 not yet removed from the annularly shaped planar disc of the head overlay element 712.

Reference is now had to FIGS. 8-12 for a description of one configuration of the rim of the head overlay element 712 that automatically accommodates either a stethoscope head of a first given diameter or another stethoscope having a larger diameter than the stethoscope head having the first given diameter. As seen in FIGS. 8 and 9, each of which is an enlarged perspective view of this one configuration of the rim of the head overlay element 712, the rim includes a first pair of diametrically opposed locking tabs 750 and a second pair of diametrically opposed locking tabs 752 that extend radially inwardly. The first pair of diametrically opposed locking tabs 750 and the second pair of diametrically opposed locking tabs 752 are configured to resiliently yield radially outwardly when the stethoscope head having the first given diameter is seated into the rim. The rim also includes a third pair of diametrically opposed locking tabs 754 that extend radially inwardly and which are configured to resiliently yield radially outwardly when the larger stethoscope head having a diameter greater than the stethoscope head having the first given diameter is seated in the rim. FIG. 10 is a top plan view of the one configuration of the rim of the head overlay element 712 shown in FIGS. 8 and 9. FIG. 11, which is a sectional view of the one configuration of the rim of the head overlay element 712 shown in FIG. 10 taken along lines AL-AL, shows first pair of diametrically opposed locking tabs 750. FIG. 12, which is a sectional view the one configuration of the rim of the head overlay element 712 shown in FIG. 10 taken along lines BL-BL, shows third pair of diametrically opposed locking tabs 754. It can also be seen that the one configuration of the rim of the head overlay element 712 has a suitable recess for accommodating the connector tube 514 of the stethoscope 510 and, as desired, another identical recess can be provided in diametric opposition so that the cover assembly 710 can be readily deployed in a left hand or right hand seating configuration on a stethoscope.

Figure 13:
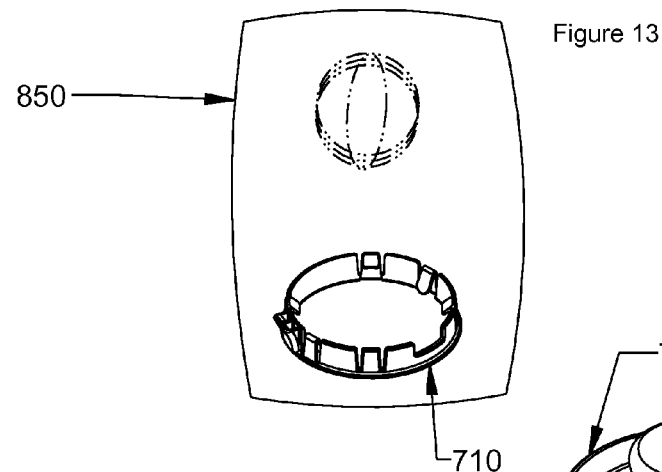
FIG. 13 is a perspective view of a storage package containing one unit of the cover assembly of the present invention.

As seen in FIG. 13, which is a perspective view of a storage package containing one unit of the cover assembly of the present invention, a storage package 850 can be provided for packaging of a single unit of the cover assembly 710. The storage package 850 can be formed, for example, from hand tearable aluminum foil.

Figure 14:
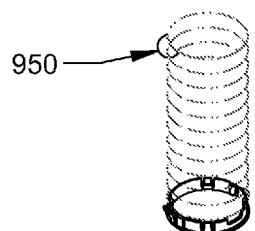
FIG. 14 is a perspective view of an extended coverage variation of the cover component of the present invention.
Figure 15:
FIG. 15 is a perspective view of the extended coverage variation of the cover component of the present invention shown in FIG. 14 deployed on a stethoscope.
Figure 16:
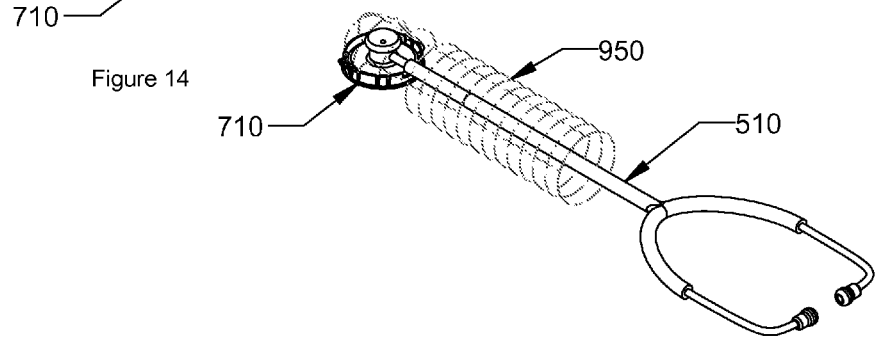
FIG. 16 is a perspective view of a stethoscope and the extended coverage variation of the cover component of the present invention, shows the extended coverage variation of the cover component of the present invention prior to its deployment on the stethoscope.
Figure 17:
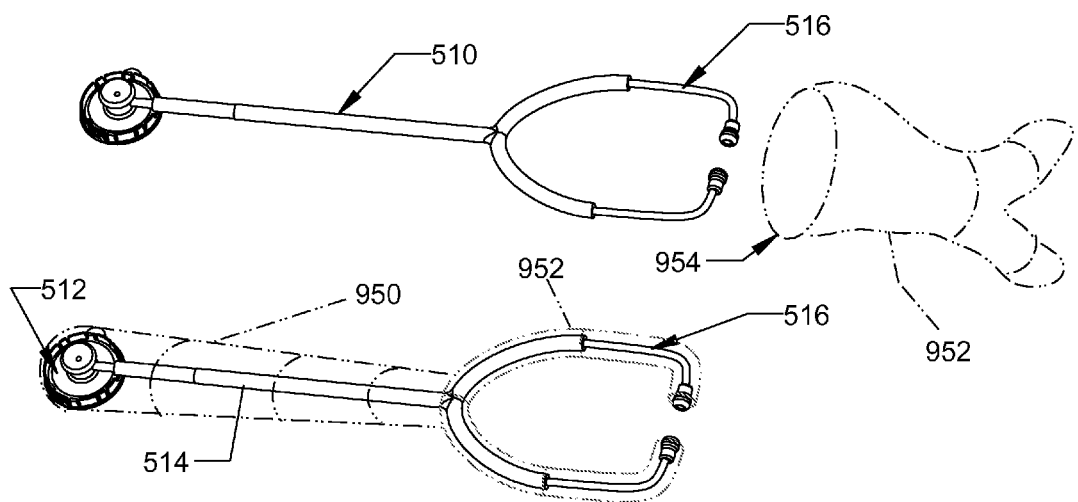
FIG. 17 is a perspective view of a stethoscope and the extended coverage variation of the cover component of the present invention, shows the extended coverage variation of the cover component of the present invention deployed on the stethoscope.

Reference is now had to FIG. 14, which is a perspective view of an extended coverage variation of the cover component of the present invention, and to FIG. 15, which is a perspective view of the extended coverage variation of the cover component of the present invention shown in FIG. 14 deployed on a stethoscope. The extended coverage variation of the cover component of the present invention includes an accordion tube sheath 950 having one end connected to the cover assembly 710 and an ear piece cover portion 952. The accordion tube sheath 950 overlies the connector tube 514 extending from the stethoscope head 512 and the ear piece cover portion 952 overlies the two ear tubes 516 extending from the connector tube 514 of the stethoscope 510. FIG. 16, which is a perspective view of a stethoscope and the extended coverage variation of the cover component of the present invention, shows the extended coverage variation of the cover component of the present invention prior to its deployment on the stethoscope. FIG. 17, which is a perspective view of a stethoscope and the extended coverage variation of the cover component of the present invention, shows the extended coverage variation of the cover component of the present invention deployed on the stethoscope. For convenience or flexibility, the head cover element 712, the accordion tube sheath 950, and the ear piece cover portion 952 can be each manufactured as separate pieces and can each be stored separately. In this configuration, suitable connecting arrangements such as, for example, elastic bands 954, can be provided to permit the head cover element 712, the accordion tube sheath 950, and the ear piece cover portion 952 to be interconnected to one another so that these interconnected components provide a completely or substantially completely sealed enclosure for the stethoscope head 510.

Figure 18:
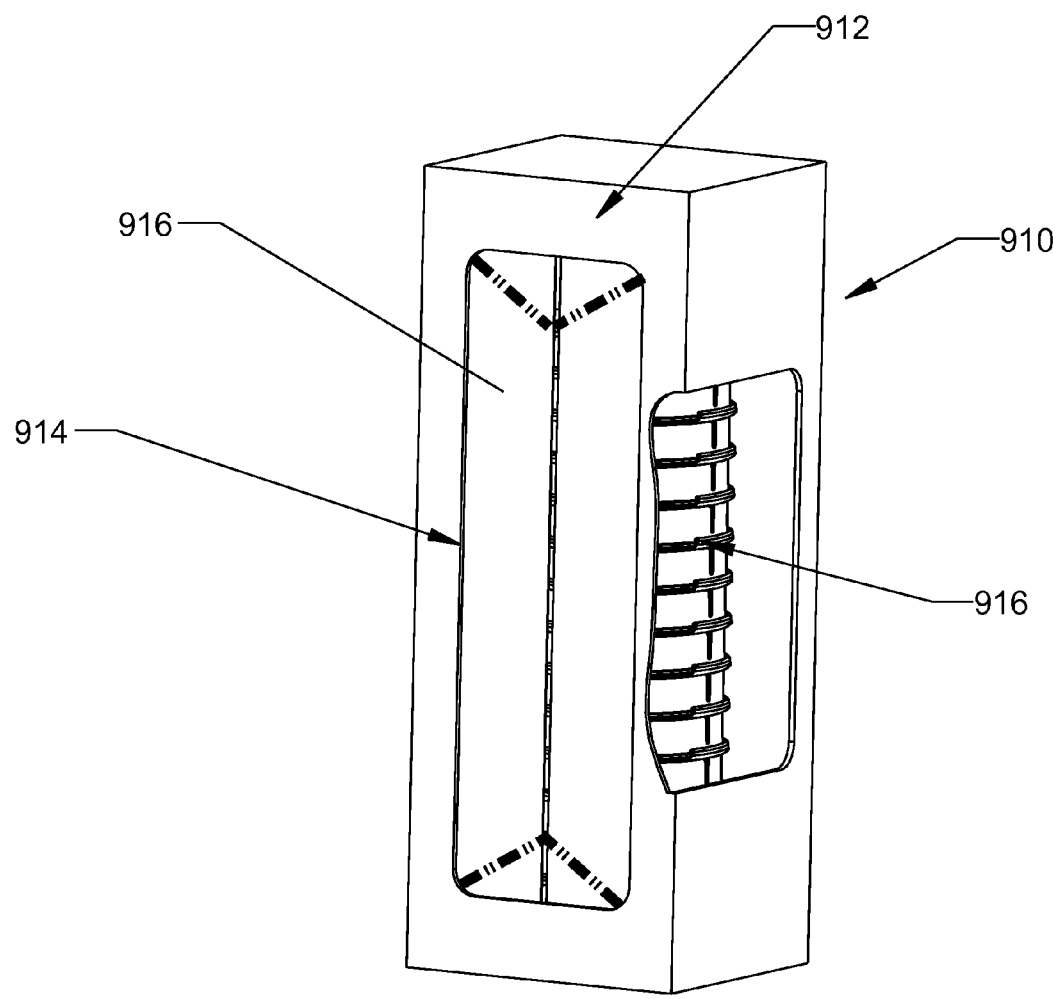
FIG. 18 is a top perspective view of an additional embodiment of a dispenser kit of the present invention configured for repeatedly individually dispensing a single unit of the cover assembly of the present invention or dispensing multiple units of the cover assembly of the present invention in a groupwise manner.
Figure 20:
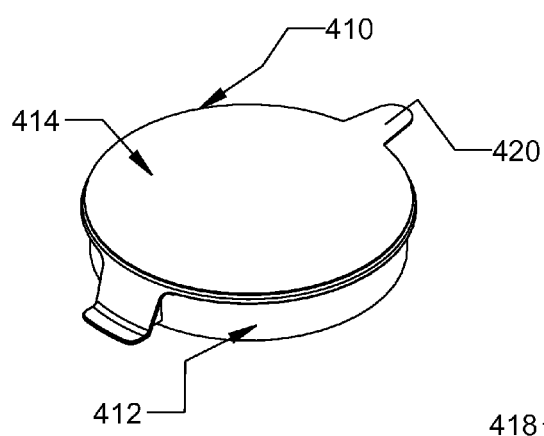
FIG. 20 is a perspective view of the further embodiment of the cover assembly of the present invention shown in FIG. 19 and showing the pre-deployment protection component in its paired disposition with the head overlay element.

As seen in FIG. 18, which is a top perspective view of an additional embodiment of a dispenser kit of the present invention configured for repeatedly individually dispensing a single unit of the cover assembly of the present invention or dispensing multiple units of the cover assembly of the present invention in a group wise manner, a dispenser kit 910 has a housing 912 having an overall rectangular box shape. An elongate opening 914 permits access to the interior of the housing 912 and is overlaid by a split screen 916 that has a pair of pliable wings slightly overlapped with one another. One or more replaceable supply cartridges 918, each retaining multiple units of the cover assembly, are accommodated within the housing 912. Accordingly, a user can access the supply cartridges 918 via the split screen 916 to remove one or multiple units of the cover assembly.

Figure 19:
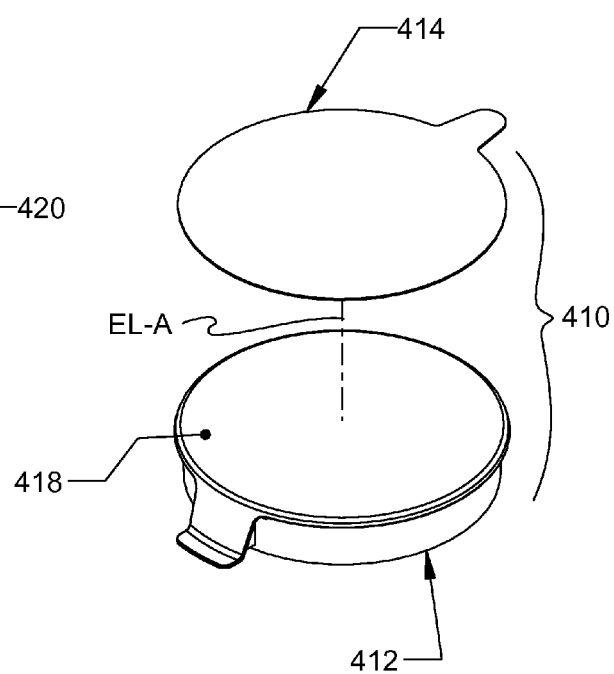
FIG. 19 is an exploded perspective view of a further embodiment of the cover assembly of the present invention.

As seen in FIG. 19, which is an exploded perspective view of another embodiment of the cover assembly of the present invention, a cover assembly generally designated as a cover assembly 410 is configured for use with a stethoscope or the type having a stethoscope head with a membrane, a sound transmission tube extending from the stethoscope head, and an ear placement piece connected to the sound transmission tube. The cover assembly 410 includes a head overlay element 412 and a pre-deployment protection component 414.

With continuing reference to FIG. 19, the head overlay element 412 is operable to overlay the stethoscope head 512 in the deployed disposition of the cover assembly 410 in which the cover assembly 410 is releasably retained on the stethoscope 510. The head overlay element 412 has an element axis EL-A and, as seen in FIG. 4B, a head facing surface 416. With reference again to FIG. 19, the cover assembly 410 also includes a stand off surface 418. The head facing surface 416 of the head overlay element 412 is axially intermediate the stethoscope head 512 and the stand off surface 418 of the head overlay element 512 in the deployed disposition of the cover assembly 410.

With further reference to FIG. 19, the pre-deployment protection component 414 of the cover assembly 410 is operably associated with the head overlay element 412 and is operable to discourage the deposition of certain substances on the head overlay element 412. The pre-deployment protection component 414 is located relative to the head overlay element 412 such that the stand off surface 418 of the head overlay element 412 is axially intermediate the pre-deployment protection component 414 and the head facing surface 416 of the head overlay element 412.

Details will now be provided of one possible configuration of the cover assembly 410 shown in FIG. 19 that is suitable for producing a mass-production unit produced according to conventional manufacturing mass production techniques. This configuration of the cover assembly 410 is described and illustrated herein solely for the purpose of providing an exemplary configuration of the cover assembly of the present invention and the method of manufacture, the material construction, the dimensions, and the other properties of this mass-production unit of the cover assembly 410 are not intended to be considered as limitations on the present invention. In connection with this mass-production unit of the cover assembly 410, the head overlay element 412 of the cover assembly 410 is produced as a single piece comprised of a polymeric substance or plastic and molded or cast via a conventional plastic injection molding process, thermo-forming process, or any other suitable process.

Figure 21:
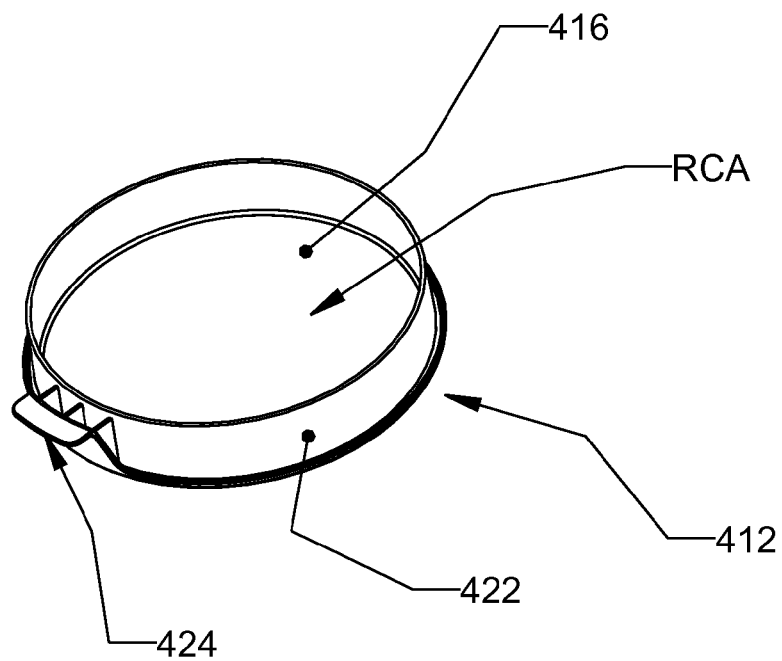
FIG. 21 is a perspective view of the head overlay element with its head facing surface being visible.
Figure 22:
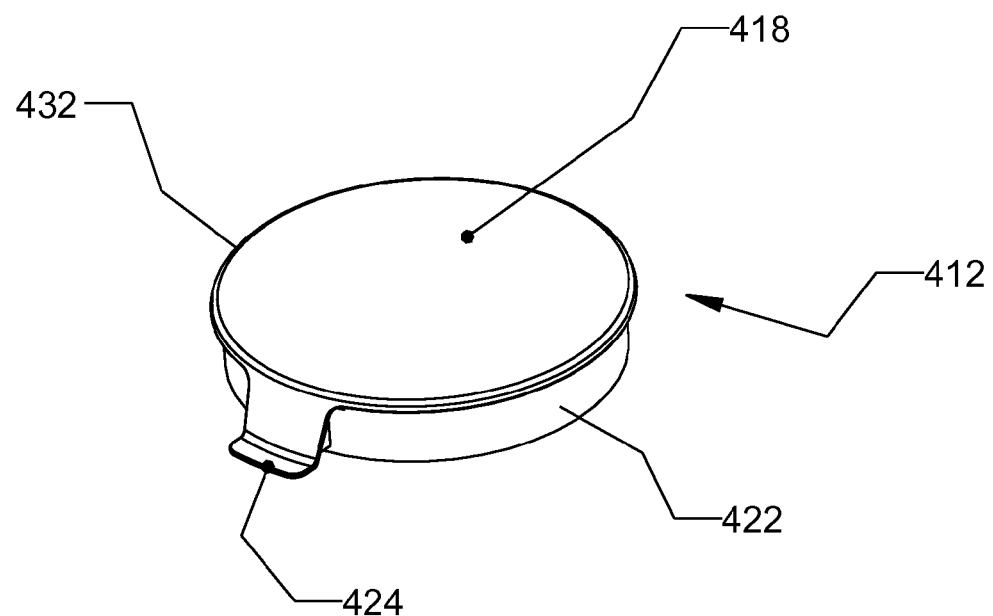
FIG. 22 is a perspective view of the head overlay element with its stand off surface being visible.

As seen in FIG. 21 which is a perspective view of the head overlay element 412 with its head facing surface 416 being visible, the head overlay element 412 delimits a receipt chamber RCA in which the stethoscope head 512 is received in the deployed disposition of the cover assembly 410 and the receipt chamber RCA has a sidewall 422 extending peripherally around the element axis EL-A. The sidewall 422 extends axially and forms a complete annular loop. The head facing surface 416 of the head overlay element 412 delimits a floor of the receipt chamber RCA in this mass-production unit of the cover assembly 410. As seen in FIG. 22, which is a perspective view of the head overlay element 412 with its stand off surface 418 being visible, the stand off surface 418 of the head overlay element 412 is in the shape of a circular disk. As seen in FIG. 23, which is a bottom plan view of the head overlay element 412, the head facing surface 416 of the head overlay element 412 is in the shape of a circular disk. The head overlay element 412 includes a detent 424 operable to be engaged by a finger of the health care assessor in a manner that facilitates seating of the head overlay element 412 on the stethoscope head 512 or, alternatively, in a manner that facilitates unseating the head overlay element 412 from the stethoscope head 512. The detent 424 includes a fingertip rest 426 that is supported radially outwardly from the sidewall 422 by a pair of arms 428.

As seen in FIG. 24, which is a sectional side view of the head overlay element 412 shown in FIG. 23 take along Line A-A and, as FIG. 25, which is an enlarged sectional view of a portion of the head overlay element 412 shown in FIG. 24, the fingertip rest 426 of the detent 424 has a planar angular extent parallel to the head facing surface 416 and the stand off surface 418 and the fingertip rest 426 is dimensioned and secured to the pair of arms 428 in correspondence with these arms such that these arms resiliently yield radially inwardly when a radially inward force is applied by, for example, the finger of a health care assessor, on the fingertip rest 426. The radial inward yielding of the arms 426 is configured such that these arms transmit the radially inward force is applied on the fingertip rest 426 to the sidewall 422 and thereby cause a distortion of the sidewall 422 from its nominal annular shape, thus facilitating an unseating of the head overlay element 412 from the stethoscope head 512.

With further reference to FIG. 25, the head overlay element 412 also includes an annular rib 430 projecting radially inwardly from the inner surface of the sidewall 422 at an axial spacing from the head facing surface 416. The inner diameter of the annular rib 430 is configured in correspondence with the outer diameter of the annular sidewall of the stethoscope head 512 such that the annular rib 430 of the head overlay element 412 has a slightly smaller diameter than the outer diameter of the annular sidewall of the stethoscope head 512. Accordingly, the annular rib 430 of the head overlay element 412 exerts a resiliently yieldable radially inwardly directed force on the stethoscope head 512 when the head overlay element 412 is moved axially relative to the stethoscope head 512 and the annular sidewall of the stethoscope head 512 exerts a radially outward force on the annular rib 430, whereby the annular rib 430 of the head overlay element 412 facilitates the retention of the cover assembly 410 on the stethoscope head 512 in the deployed disposition of the cover assembly 410 on the stethoscope head 512. The head overlay element 412 further includes an annular rim 432 extending annularly and delimiting the outer diameter of the head overlay cement 412.

Figure 26:
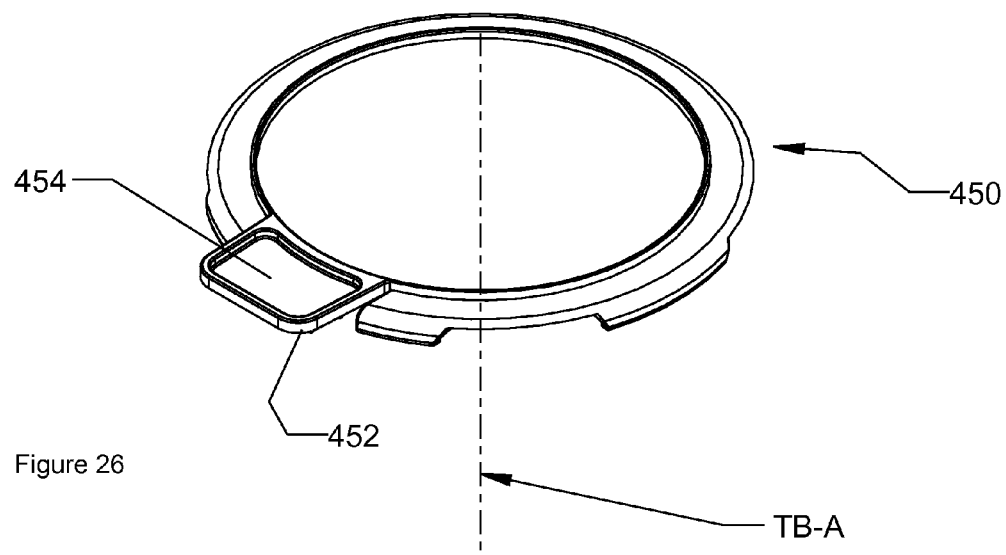
FIG. 26 is a top perspective view of the pre-deployment protection component.
Figure 27:
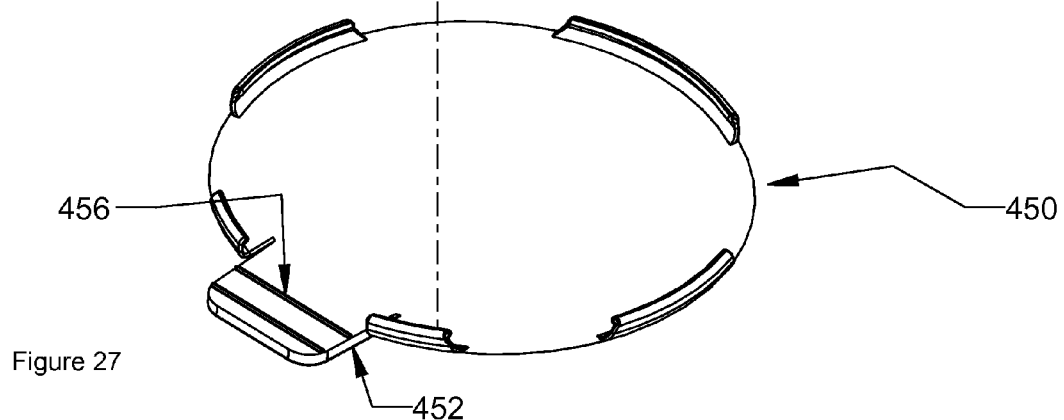
FIG. 27 is a bottom perspective view of the pre-deployment protection component.

Turning now to the configuration of the pre-deployment protection component 414 of the exemplary mass-production unit of the cover assembly 410, this configuration of the pre-deployment protection component 414 is hereinafter referred to as the tab plate 450, and details of the tab plate 450 are shown in FIG. 26, which is a top perspective view of the tab plate 450, FIG. 27, which is a bottom perspective view of the tab plate 450, FIG. 28, which is a bottom plan view of the tab plate 450, FIG. 29, which is a sectional side view of the tab plate 450 shown in FIG. 28 taken along line B-B and FIG. 30, which is an enlarged side view of a portion of the tab plate 450 shown in FIG. 29. The tab plate 450 is formed of polymeric material or plastic having sufficient rigidity to have a shape memory property in that the tab plate 450 distorts from its original nominal shape upon the application of certain shape distorting forces thereagainst and returns to its original nominal shape a cessation of the certain shape distorting forces. In this connection, and additionally in connection with providing the tab plate 450 with a beneficial property of retarding the passage of the certain organisms through the tab plate 450, the tab plate 450 may be formed of a medical grade polymeric material such as, for example, a material distributed under the registered trademark Santoprene.

The tab plate 450 includes a force applying area at which a force can be exerted on the tab plate 450 to promote disengagement of the tab plate 450 from the head overlay element 412 and this force applying area is configured as a pull leaf 452 extending radially outwardly. As seen in FIG. 26, the pull leaf 452 has, on a top side thereof, a recessed thumb rest 454 configured for engagement by the tip of a thumb of a health care assessor and, on a bottom side thereof, a pair of ridges 456, as seen in FIG. 27, configured for engagement by a finger of the health care assessor when the health care assessor grasps the pull leaf 452 with a thumb and a respective finger pressing toward one another. The tab plate 450 is formed with a circular display surface 458 on which text or visual instructions or trademarks may be displayed. For example, a text instruction in the form of the word "disposable" can be imprinted or embossed on the circular display surface 458. The circular display surface 458 is centered on a tab plate axis TB-A and the outer diameter of the circular display surface 458 is delimited by an annular stacking rib 460 that extends axially outwardly and forms one axial end of the tab plate 450.

Figure 31:
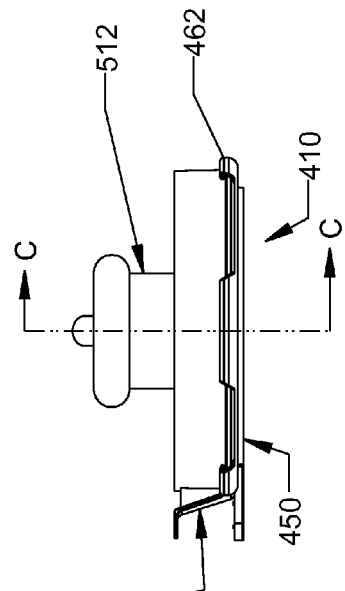
FIG. 31 is a side elevational view of the cover assembly in its deployed disposition on the stethoscope head.
Figure 32:
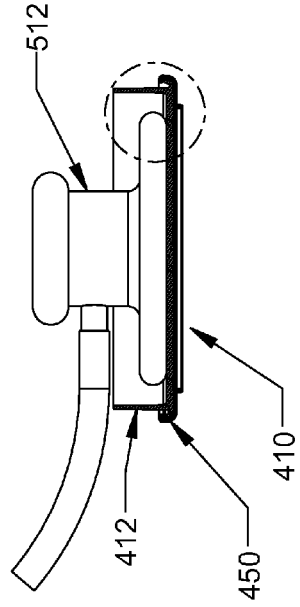
FIG. 32 is a sectional side elevational view of the cover assembly in its deployed disposition on the stethoscope head taken along line C-C in FIG. 31.

The tab plate 450 also includes a plurality of arc segments 462 each of which subtends a respective angular portion of the outer diameter of the tab plate. The arc segments 462 each extend axially in an axial direction opposite to the annular stacking rib 460. Each arc segment 462 includes a lap over rib 464 extending radially inwardly and dimensioned in correspondence with the outer diameter of the head overlay element 412 such that the lap over ribs of the arc segments 462 of the tab plate 450 releasably retain the tab plate on the head overlay element 412 when the tab plate 453 is disposed in an interlock disposition with the head overlay element 412. As seen in FIG. 31, which is a side elevational view of the cover assembly 410 in its deployed disposition on the stethoscope head 512, and FIG. 32, which is a sectional side elevational view of the cover assembly 410 in its deployed disposition on the stethoscope head 512 taken along line C-C in FIG. 31, the head overlay element 412 and the tab plate 450 are configured to be interlocked with one another so as to comprise a single sub-assembly for convenient deployment onto the stethoscope head 512.

Figure 33:
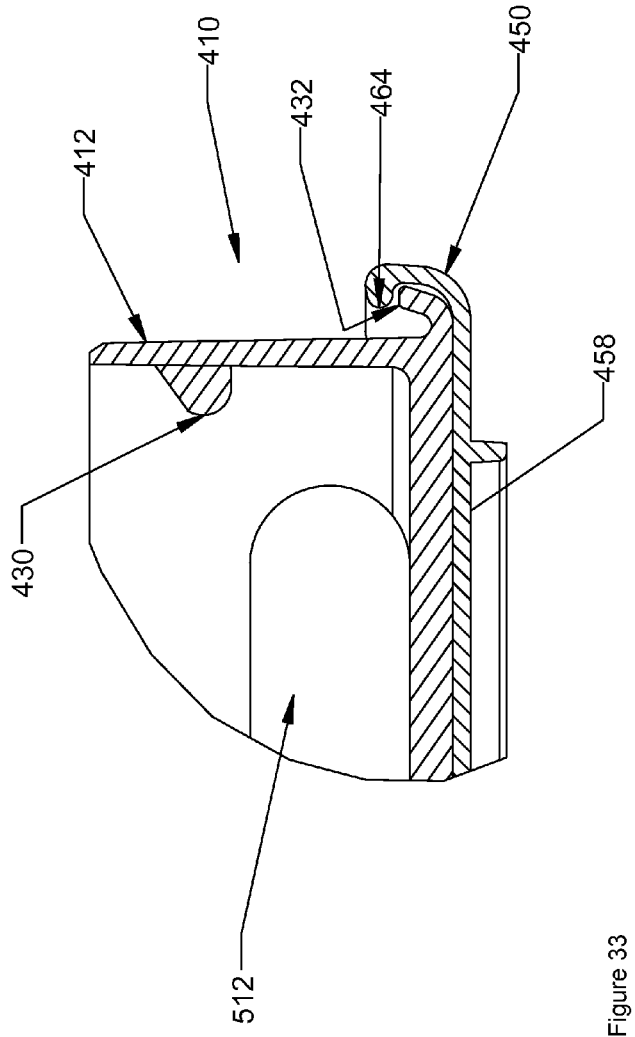
FIG. 33 is an enlarged sectional side elevational view of a portion of the cover assembly and the stethoscope head shown in FIG. 32.

In the interlock disposition of the tab plate 450 with the head overlay element 412, the tab plate axis TB-A of the tab plate 450 and the element axis EL-A are co-axial with one another and the tab plate 450 is seated on the head overlay element 412 such that, when the cover assembly 410 is in its deployed disposition on the stethoscope head 512, the circular display surface 458 of the tab plate 450 faces axially outwardly and the head overlay element 412 is axially intermediate the tab plate 450 and the stethoscope head 512. The respective releasable securement of the tab plate 450 to the head overlay element 412 via the action of the lap over ribs 464 of its arc segments 462 and the respective releasable securement of the cover assembly 410 to the stethoscope head 512 can be seen to good effect in FIG. 33, which is an enlarged sectional side elevational view of a portion of the cover assembly 410 and the stethoscope head 512 shown in FIG. 32. The annular rim 432 of the head overlay element 412 extends radially outwardly slightly beyond the inner diameter of the lap over ribs 464 of the arc segments 462 of the tab plate 450, whereupon, to remove the tab plate 450 from the head overlay element 412, the tab plate 450 must be moved axially until the arc segments 462 of the tab plate 450 are pushed radially outwardly by the annular rim 432 of the head overlay element 412 as these arc segments 482 of the tab plate 450 move over the annular rim 432 of the head overlay element 412.

It can be understood that the tab plate 450 is at least radially co-extensive with the stand off surface 418 of the head overlay element 412, whereupon the tab plate 450 is well suited to serve as a barrier to prevent the passage of certain substances therethrough, that would otherwise be deposited on the stand off surface 418 of the head overlay element 412. For example, moisture in the form of water droplets or vapor may be effectively screened away by the tab plate 450 so that the stand off surface 418 of the head overlay element 412 is already in a suitable moisture condition (i.e., substantially dry) when the health care assessor removes the tab plate 450 and then deploys the stand off surface 418 of the head overlay element 412 directly on the skin of a patient. Moreover, the tab plate 450 may beneficially serve to intercept certain bacteria or pathogens that would otherwise be deposited on the stand off surface 418 of the head overlay element 412, thereby sparing the health care assessor from the task of neutralizing any deposited bacteria or pathogens before deploying the stand off surface 418 of the head overlay element 412 directly on the skin of a patient.

Taking consideration of the beneficial purposes of the tab plate 450, it can be understood that the tab plate 450 can be configured in various ways while still providing its several advantages. For example, in lieu of configuring the tab plate 450 as a relatively rigid piece, the tab plate 450 can be configured as a relatively non-rigid piece which, upon being disposed in contact with the stand off surface 418 of the head overlay cement 412, benefits from the relatively more rigid structure of the head overlay element 412 to resist tearing, creasing, or any partial or full unintended uncoupling from the head overlay element 412. Certain materials may be considered to render the tab plate 450 as a relatively non-rigid piece including, for example, polymeric materials, glass fiber reinforced material, coated or non-coated paper, polyethylene, or rubber. Additionally, the tab plate 450 can be removably secured to the head overlay element 412 via a different mechanism than the retention mechanism provided by the arc segments 462. For example, the arc segments 462 can be omitted and an adhesive material in contact with both the tab plate 450 and the stand off surface 418 of the head overlay element 412 can removably adhere the tab plate 450 to the stand off surface 418 of the head overlay element 412.

The ease of removing the tab plate 450 from the head overlay element 412 can be configured in correspondence with a desired mix of convenience of removal, assurance against inadvertent removal, environmentally friendly disposal considerations, and ensuring that the tab plate 450 serves its intended barrier purpose. Thus, for example, an adhesive material can be selected whose adherence performance can be overcome via manual lifting of the tab plate 450 while the head overlay element 412 is restrained against the lifting force (convenience of removal), whose adherence performance continues to maintain the tab plate 450 in a covering disposition on the stand off surface 418 of the head overlay element 412 (assurance against inadvertent removal), which is formed of a biodegradable material (environmentally friendly disposal considerations), and whose adherence performance does not unacceptably degrade when exposed to certain substances that may contact the cover assembly (ensuring that the tab plate 450 serves its intended barrier purpose).

Figure 34:
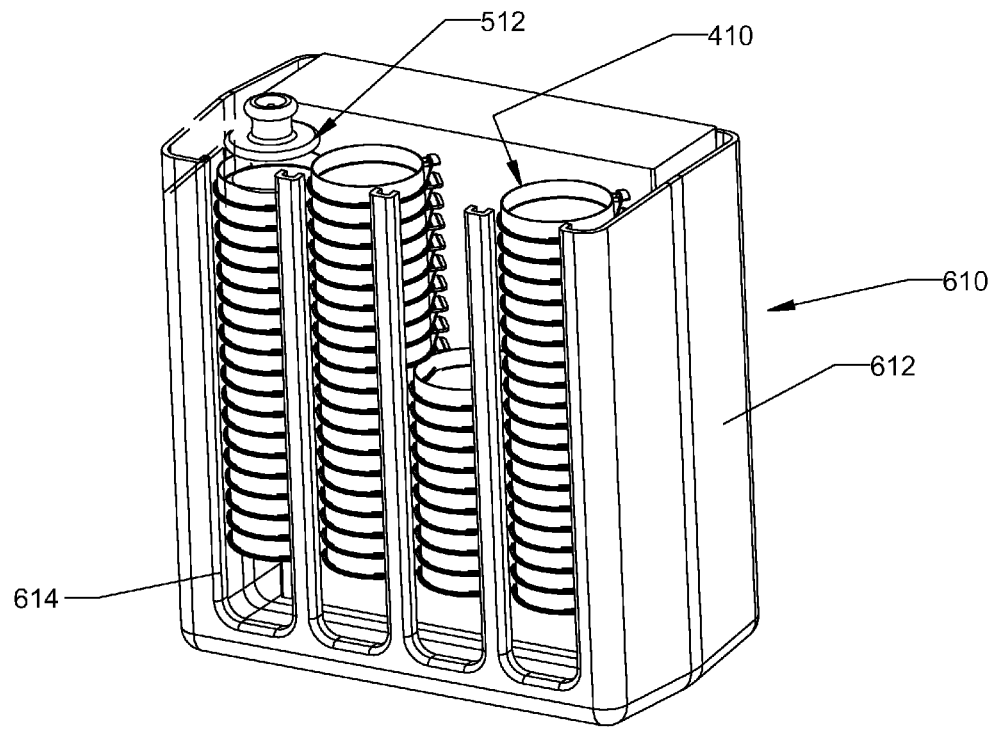
FIG. 34 is a top perspective view of one embodiment of a dispenser kit of the present invention configured for repeatedly individually dispensing a single unit of the cover assembly of the present invention or dispensing multiple units of the cover assembly of the present invention in a groupwise manner.

The configuration of the tab plate 450 as a relatively rigid piece, coupled with the configuration of the head overlay element 412 with a relatively rigid self-standing sidewall, advantageously render the cover assembly into a unit that is amenable to convenient individual or group wise dispensing. In this connection, the present invention also provides a dispenser kit that advantageously retains several units of the cover assembly on a building wall, a door, or on a furniture top surface. As seen in FIG. 34, which is a top perspective view of one embodiment of a dispenser kit of the present invention configured for repeatedly individually dispensing a single unit of the cover assembly of the present invention or dispensing multiple units of the cover assembly of the present invention in a group wise manner, a dispenser kit 610 has a housing 612 having an overall rectangular box shape and having a plurality of vertical chutes 614 each closed at its lower end, open at its top end, and having a open longitudinal slot. Each vertical chute 614 is configured in correspondence with the outer dimensions of the cover assembly such that multiple units of the cover assembly can be stacked one on the other in the vertical chute.

Figure 35:
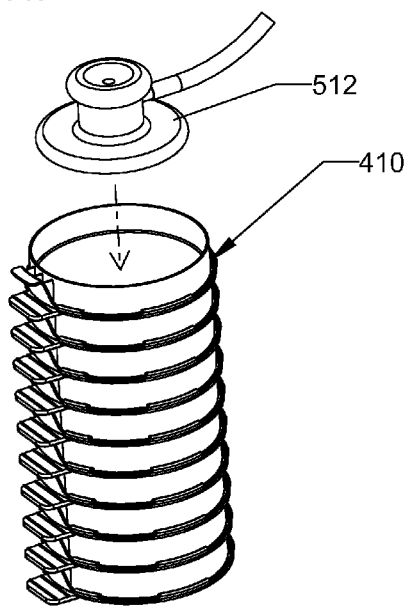
FIG. 35 is a top perspective view of a stethoscope head aligned with a column of multiple units of the cover assembly of the present invention retained in a vertical chute of the dispenser kit shown in FIG. 34.
Figure 36:
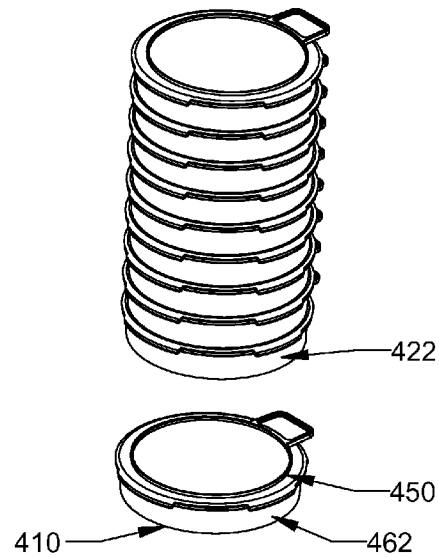
FIG. 36 is a bottom perspective view of the column of multiple units of the cover assembly of the present invention retained in a vertical chute of the dispenser kit shown in FIG. 35.

The open top end of each vertical chute 614 permits a health care assessor to easily orient the stethoscope head 512 of the stethoscope 510 relative to the stacked units of the cover assembly such that a downward movement of the stethoscope head 512 seats into and is received in the receipt chamber RCA of the topmost one of the stack of the cover assemblies, such as is illustrated in FIG. 35, which is a top perspective view of a stethoscope head aligned with a column of multiple units of the cover assembly of the present invention retained in a vertical chute of the dispenser kit shown in FIG. 34. As seen in FIG. 36, which is a bottom perspective view of the column of multiple units of the cover assembly of the present invention retained in a vertical chute of the dispenser kit shown in FIG. 35, the annular stacking rib 460 that extends axially outwardly and forms one axial end of the tab plate 450 can facilitate the stacking of units of the cover assemblies on one another if the inner diameter of the annular stacking rib 460 in compatibly configured with respect to the outer diameter of the sidewall 422 of the head overlay element 412. This permits the units of the cover assemblies disposed in a vertical chute 614 to be stacked one on the other with the tab plate 450 of the cover assemblies facing downward, whereupon the upright sidewall 422 of each cover assembly unit will be seated within the annular stacking rib 460 of the tab plate 450 of the adjacent next higher cover assembly unit.

Figure 37:
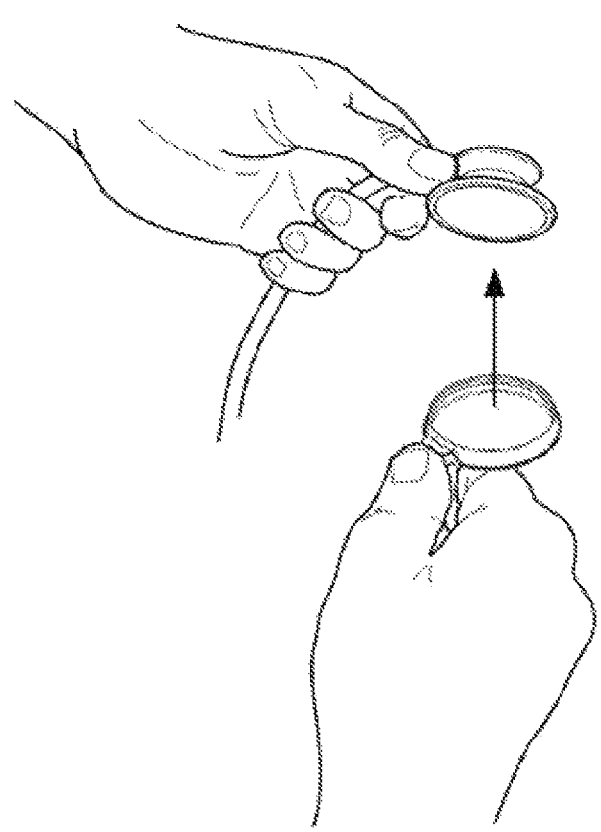
FIG. 37 is a perspective view of the stethoscope head being stationarily maintained while grasped by one hand of a health care assessor and the cover assembly unit grasped by the other hand of the health care assessor and oriented below the stethoscope head for subsequent upward movement of the cover assembly unit to seat the cover assembly unit on the stethoscope head.
Figure 38:
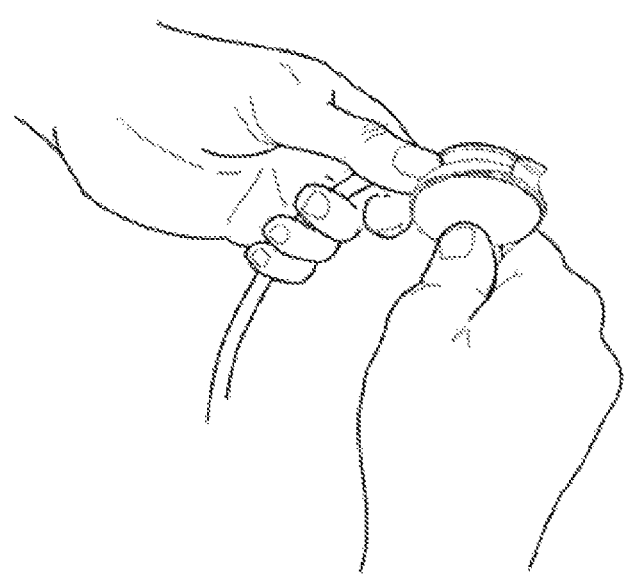
FIG. 38 is a perspective view of the cover assembly shown in FIG. 37 after it has been seated on the stethoscope head.

The vertical chutes 614 of the dispenser kit 610 permit the individual dispensing of a single cover assembly unit to a health care assessor. The health care assessor can orient and then seat the stethoscope head 512 on the topmost cover assembly unit, such as is shown in FIG. 35, or the health care assessor can grasp and extract the topmast cover assembly unit and then manually dispose the cover assembly unit on the stethoscope head 512, such as is illustrated in FIG. 37, which is a perspective view of the stethoscope head being stationarily maintained while grasped by one hand of a health care assessor and the cover assembly unit grasped by the other hand of the health care assessor and oriented below the stethoscope head for subsequent upward movement of the cover assembly to seat the cover assembly on the stethoscope head, and FIG. 38, which is a perspective view of the cover assembly shown in FIG. 37 after it has been seated on the stethoscope head. The health care assessor can also readily grasp and withdraw several cover assembly units in a vertical chute 614 with a single hand and then place the dispensed cover assembly units in a convenient location such as, for example, a pocket of clothing worn by the health care assessor, whereupon these cover assembly units are conveniently available to the health care assessor to replace each cover assembly unit on the stethoscope head 512 with a fresh cover assembly unit after each patient monitoring session.

Figure 39:
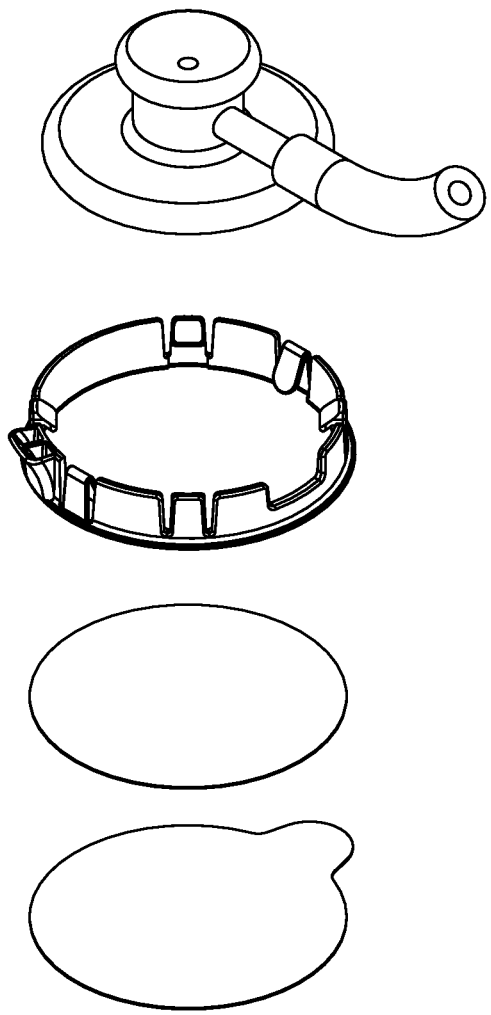
FIG. 39 is a perspective exploded view of the stethoscope head and a cover assembly unit oriented below the stethoscope had for subsequent upward movement of the cover assembly unit to seat the cover assembly unit on the stethoscope head.

The ease of use of the cover assembly of the present invention is clearly seen in FIG. 39, which is a perspective exploded view of the stethoscope head and a cover assembly unit oriented below the stethoscope head for subsequent upward movement of the cover assembly unit to seat the cover assembly unit on the stethoscope head. The configuration is convenient to both carry in a pocket or the like for later deployment on a stethoscope head and to easily and reliably seat the cover assembly on the stethoscope head. Moreover, the tab plate design advantageously overlies the head overlay element until the cover assembly unit is ready for its role in covering the stethoscope head and this tab plate can be conveniently removed and is amenable to a configuration that is environmentally friendly both in its material composition and its very slight weight and volume disposal requirements.

The exemplary shapes, dimensions, and materials described herein are provided by way of example only. Cover assemblies for stethoscopes fabricated in different shapes or dimensions and comprised of different features and materials other than those discussed and illustrated herein also are contemplated as being within the scope of the present invention.

Although this invention has been disclosed and described in its preferred forms with a certain degree of particularity, it is to be realized that the optimum dimensional relationships for the parts of the invention, to include variations in size, materials, shape, form, function and manner of operation, assembly and use, are deemed readily apparent and obvious to one skilled in the art. Additionally, it is understood that the present disclosure of the preferred forms is only by way of example and that numerous changes in the details of operation and in the combination and arrangement of parts may be resorted to without departing from the spirit and scope of the invention as hereinafter claimed.

What is claimed is:

1. A cover assembly for use with a stethoscope having a stethoscope head with a membrane, a sound transmission tube extending from the stethoscope head, and an ear placement piece connected to the sound transmission tube, the assembly comprising:
   a head overlay element, the head overlay element being operable to overlay the stethoscope head in a deployed disposition of the assembly in which the assembly is releasably retained on the stethoscope, the head overlay element having an element axis, a head facing surface and a stand off surface with the head facing surface of the head overlay element being axially intermediate the stethoscope head and the stand off surface of the head overlay element in the deployed disposition of the assembly;
   a pre-deployment protection component operably associated with the head overlay element and operable to discourage the deposition of certain substances on the head overlay element and the pre-deployment protection component being located relative to the head overlay element such that the stand off surface of the head overlay element is axially intermediate the pre-deployment protection component and the head facing surface of the head overlay element;
   the pre-deployment protection component attached to, covering, and releasably secured to, the head overlay element; and
   the cover assembly constituting a unitary two layer integrated membrane including the head overlay element and the pre-deployment protection component.

2. The cover assembly according to claim 1, wherein the pre-deployment protection component includes a force applying area at which a force can be exerted on the pre-deployment protection component to promote disengagement of the pre-deployment protection component from the head overlay element.

3. The cover assembly according to claim 2, wherein the pre-deployment protection component includes a barrier that retards the passage of the certain organisms therethrough and the barrier extends at least partially over the stand off surface of the head overlay element as viewed in the radial direction of the head overlay element.

4. The cover assembly according to claim 1, wherein the pre-deployment protection component Includes a tab extending radially outwardly of the head overlay element.

5. The cover assembly according to claim 1, wherein the head overlay element delimits a receipt chamber in which the stethoscope head is received in the deployed disposition of the assembly, the receipt chamber has a sidewall extending peripherally around the element axis and the head facing surface delimits a floor of the receipt chamber.

6. A dispenser kit from which cover assemblies for stethoscopes can be dispensed, the dispenser kit comprising:
   a housing, the housing having a chute in which a column of cover assemblies can be stored, each cover assembly being deployable on a stethoscope having a stethoscope head with a membrane, a sound transmission tube extending from the stethoscope head, and an ear placement piece connected to the sound transmission tube and each cover assembly including a unitary two layer integrated membrane having a pre-deployment protection component and a head overlay element, the head overlay element being operable to overlay the stethoscope head in a deployed disposition of the assembly in which the assembly is releasably retained on the stethoscope, the head overlay element having an element axis, a head facing surface and a stand off surface with the head facing surface of the head overlay element being axially intermediate the stethoscope head and the stand off surface of the head overlay element in the deployed disposition of the assembly, and a pre-deployment protection component operably associated with the head overlay element and operable to discourage the deposition of certain substances on the head overlay element and the pre-deployment protection component being located relative to the head overlay element such that the stand off surface of the head overlay' element is axially intermediate the pre-deployment protection component and the head facing surface of the head overlay element;
   the cover assemblies being placed within and nested in a column within the chute, the head overlay elements being in an upright position to accept insertion of a stethoscope; and
   the housing having an uppermost top access opening for removing the cover assemblies from the top of the chute in individual or group wise manner.

7. The dispenser kit according to claim 6, wherein the housing includes a plurality of chutes.

8. The dispenser kit according to claim 7, wherein each of the chutes includes an open longitudinal slot.

* * * * *